United States Patent [19]

McDonald

[11] Patent Number: 5,776,139
[45] Date of Patent: Jul. 7, 1998

[54] ROCKING LENS IMPLANTATION APPARATUS

[75] Inventor: Henry H. McDonald, 8 Whittier Ct., Rancho Mirage, Calif. 92270

[73] Assignees: Henry H. McDonald; William W. Haefliger, both of Pasadena, Calif.; a part interest

[21] Appl. No.: 800,966

[22] Filed: Feb. 18, 1997

[51] Int. Cl.$^6$ ........................................ A61F 9/00
[52] U.S. Cl. ................... 606/107; 606/210; 606/206
[58] Field of Search ............... 606/107, 205–207, 606/210, 211, 151, 161, 157

[56] References Cited

U.S. PATENT DOCUMENTS

| | | |
|---|---|---|
| 1,837,277 | 12/1931 | Lund . |
| 3,043,902 | 7/1962 | Klein .................................. 606/208 |
| 3,980,086 | 9/1976 | Kletschka et al. . |
| 4,573,998 | 3/1986 | Mazzocco . |
| 4,785,810 | 11/1988 | Baccala et al. . |
| 4,813,957 | 3/1989 | McDonald .................................. 623/6 |
| 4,844,065 | 7/1989 | Faulkner .................................. 606/107 |
| 4,873,979 | 10/1989 | Hanna .................................. 606/167 |
| 4,959,070 | 9/1990 | McDonald . |
| 5,007,913 | 4/1991 | Dulebohn et al. . |
| 5,064,429 | 11/1991 | Waterman et al. .................. 606/151 |
| 5,078,729 | 1/1992 | Eichhorn .................................. 606/210 |
| 5,178,622 | 1/1993 | Lehner, II .................................. 606/107 |
| 5,203,789 | 4/1993 | McDonald . |
| 5,203,790 | 4/1993 | McDonald . |
| 5,222,960 | 6/1993 | Poley . |
| 5,292,324 | 3/1994 | McDonald . |
| 5,425,759 | 6/1995 | McDonald . |
| 5,630,821 | 5/1997 | Klaas .................................. 606/107 |
| 5,653,753 | 8/1997 | Brady et al. .................................. 606/107 |

FOREIGN PATENT DOCUMENTS

| | | |
|---|---|---|
| 2555952 | 6/1985 | France . |
| 361627 | 10/1922 | Germany . |
| 119055 | 9/1918 | United Kingdom . |

Primary Examiner—Robert A Hafer
Assistant Examiner—Justine R. Yu
Attorney, Agent, or Firm—William W. Haefliger

[57] ABSTRACT

An apparatus used for intraocular implantation of a plastic lens in an internal eye zone, as via a surgical incision in the corneo-scleral limbus, which includes two elongated lever arms, each of which has a distal first zone for gripping the lens, a second pivot zone rearward of the distal zone, and a third manual pressure receiving zone; the arms coupled together rearwardly of the third zones so that the first distal zones are yieldably urged toward one another by the arms to grip the lens therebetween for intraocular implantation; the second pivot zones configured to pivot in interengagement in response to controllable manual squeezing force exertion on the third zones, thereby to cause the first zones to relatively separate, freeing the lens for release in the internal eye zone.

12 Claims, 4 Drawing Sheets

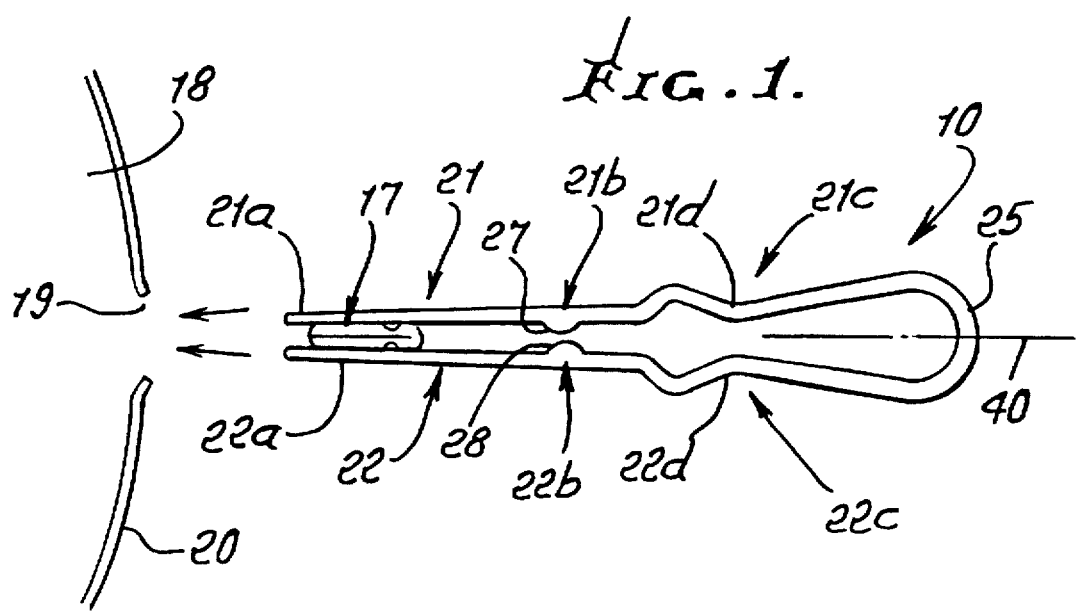
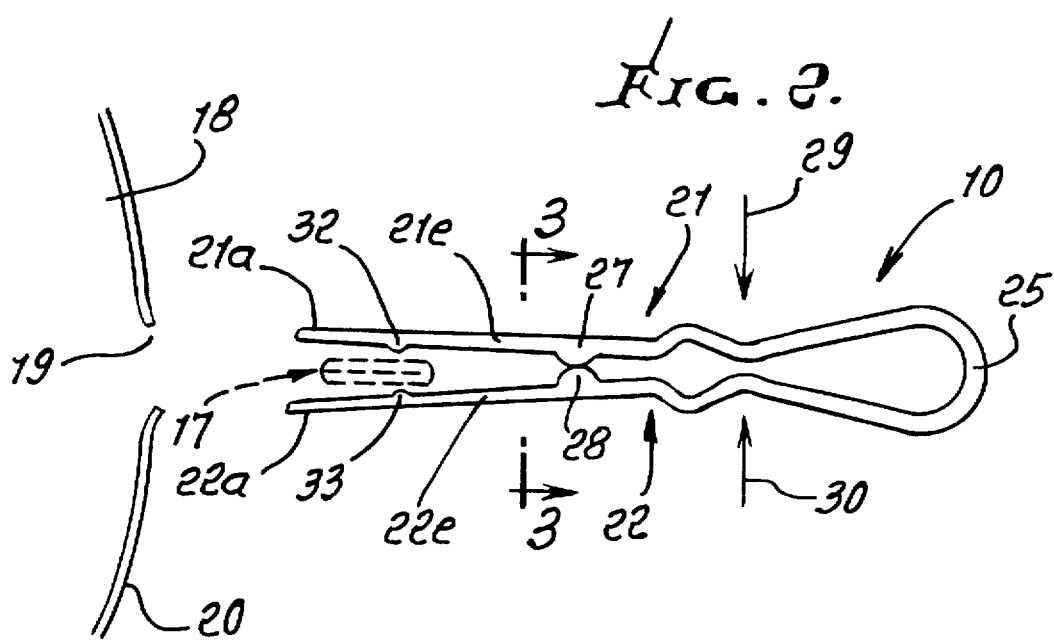
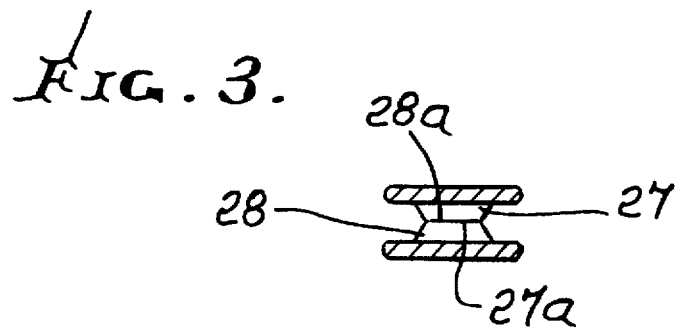

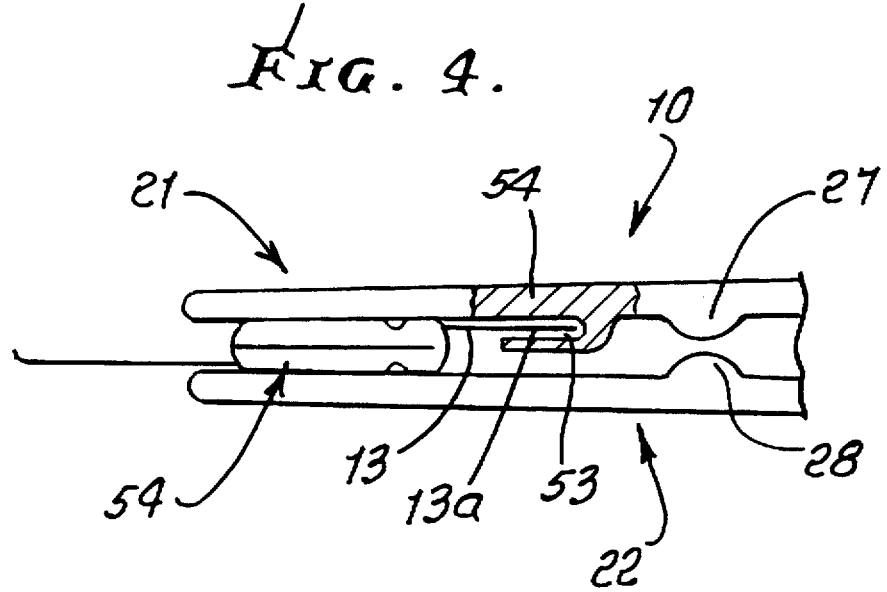
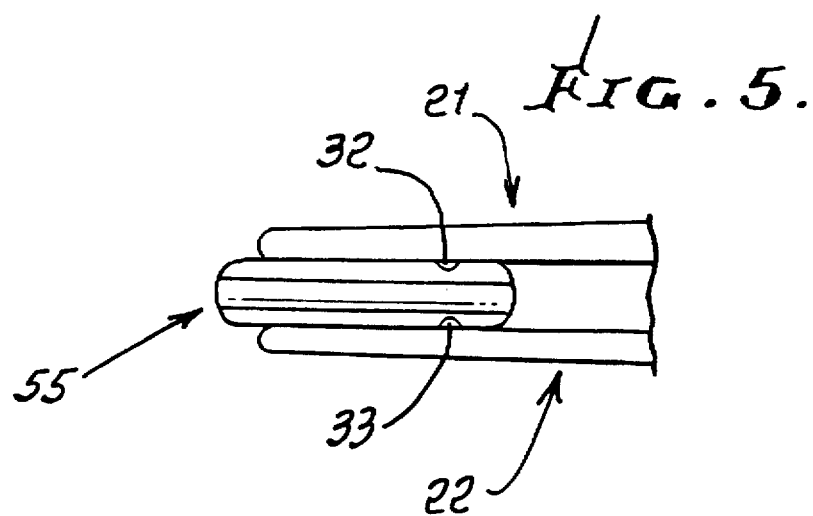

1

ROCKING LENS IMPLANTATION APPARATUS

BACKGROUND OF THE INVENTION

This invention relates generally to implantation of an artificial lens within the eye, and more specifically, concerns improvements in instruments used for this purpose.

There is need for further improvements in instrumentation used for this purpose; and in particular for improvements as are described herein, to provide unusual advantages as will appear.

SUMMARY OF THE INVENTION

It is a major object of the invention to provide improved instrumentation meeting the above-described need.

Basically, the herein-described apparatus is used for intraocular implantation of a plastic lens in an internal eye zone, as via a surgical incision in the corneo-scleral limbus, and the apparatus includes:

a) two elongated lever arms, each of which has a distal first zone for gripping the lens, a second pivot zone rearward of the distal zone, and a third manual pressure-receiving zone, b) the arms coupled together rearwardly of such third zones so that the first distal zones are yieldably urged toward one another by the arms to grip the lens therebetween for intraocular implantation, c) the second pivot zones configured to pivot in interengagement in response to controllable manual squeezing force exertion at the third zones, thereby to cause the first arm zones to relatively separate, freeing the lens for release in the internal eye zone.

As will be seen, interengageable protrusions are typically provided for projecting between the arms at the second zones, to define mutual fulcrums for arm pivoting.

It is another object to provide such protrusions that have interengageable surfaces which are convex toward one another; and wherein said protrusions are spaced apart prior to said manual squeezing force exertion at the third zones, for reasons as will appear.

Another object is to provide lever arms that have substantially the same configurations that are mirror imaged, for simplicity.

Yet another object is to provide holder surfaces on said arms, offset from the third zones, to allow a physician to hold and manipulate the apparatus without inadvertent release of the lens, and before applying squeezing force that releases the lens.

A further object is to provide for gripping of a plastic lens between the arm distal first zones; and typically, the lens may be folded in gripped condition, although the apparatus is usable for inserting non-folded lenses.

An additional object is the provision of a bow spring segment coupling the arms together, rearwardly of the described third zones, and exerting predetermined lens grip force via the arms, so that the lens squeezing is not made a variable by physician-controlled squeezing of the lens, whereby lens damage is substantially lessened.

These and other objects and advantages of the invention, as well as the details of an illustrative embodiment, will be more fully understood from the following specification and drawings, in which:

DRAWING DESCRIPTION

FIG. 1 is a side elevation showing a preferred embodiment; and a folded lens gripped by the device;

FIG. 2 is a view like FIG. 1 but showing manual force application to cause lens release;

FIG. 3 is a section taken on lines 3—3 of FIG. 2;

FIG. 4 is an enlarged fragmentary view of a modification showing retention of a haptic projecting from a lens gripped by the device;

FIG. 5 is an enlarged fragmentary view showing gripping of a lens, which has multiple folds;

FIG. 6 is a section taken through the multiple folded lens of FIG. 5;

FIG. 9, views a)–d), show progressive stages of lens release, in side view; and

Figure 10:
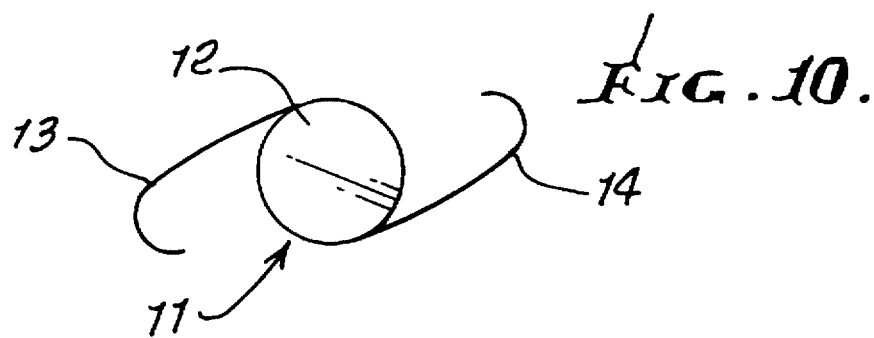
Figure 11:
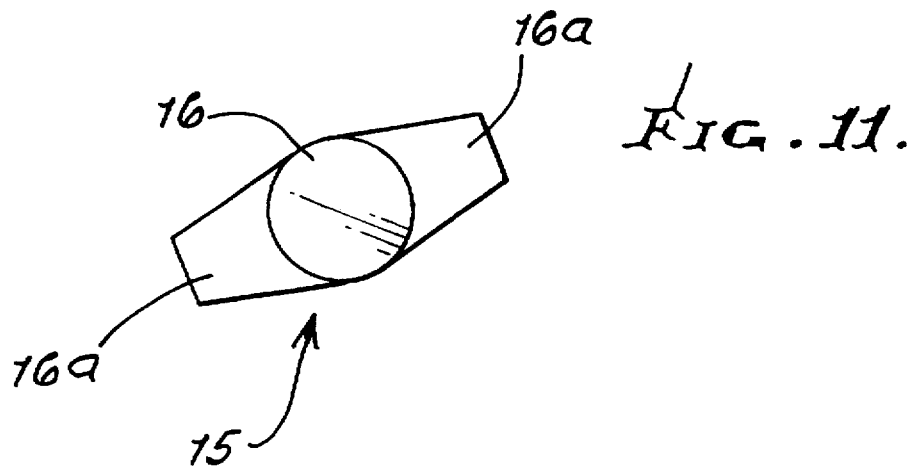
Figure 9A:
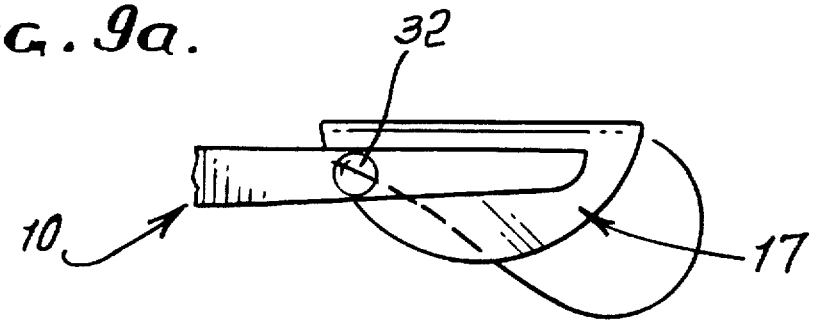
Figure 9B:
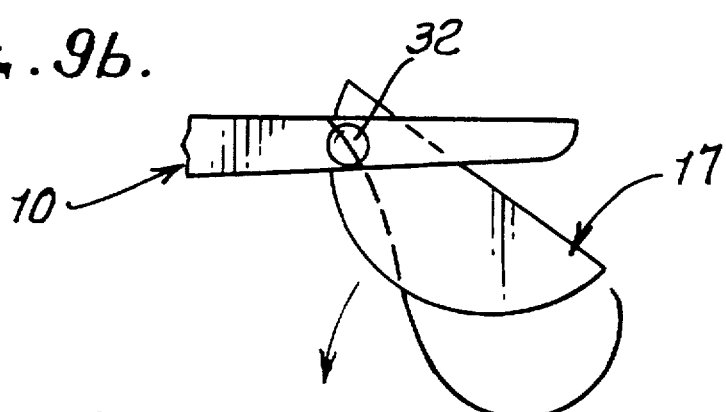
Figure 9C:
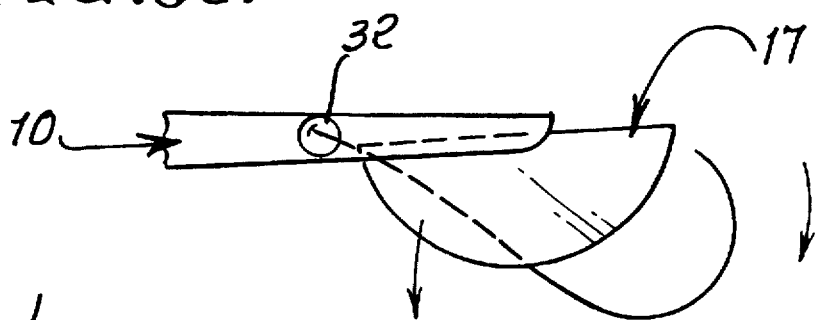
Figure 9D:
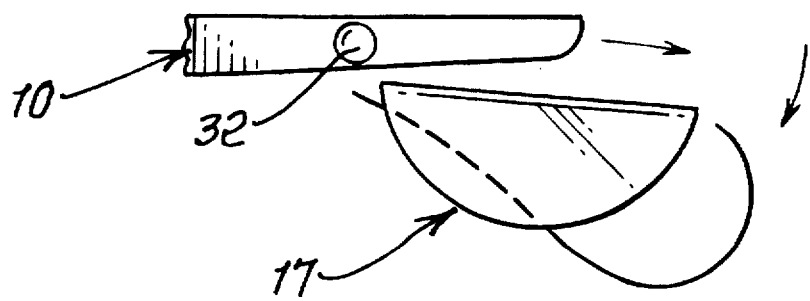

FIGS. 10 and 11 show foldable interocular plastic lenses of types that can be implanted using the described apparatus.

DETAILED DESCRIPTION

In FIGS. 1 and 2, the device or apparatus 10, i.e., instrument, is used for interocular implantation of a plastic lens. Typical lens units are shown in FIGS. 10 and 11, others being usable. See for example my U.S. Pat. Nos. 5,203,789, 5,203,790 and 5,425,759, incorporated herein by reference.

In FIG. 10, a lens unit 11 has a lens zone 12, and two filamentary haptics 13 and 14.

In FIG. 11, the lens unit 15 has a lens zone 16, and two tabular or plate-like haptics 16a, for centering the unit in the eye.

A single folded lens unit is shown at 17 in FIG. 1, to be implanted in the eye interior 18 via a surgical incision 19 in the corneo-scleral limbus 20. The folded lens is gripped between and by two elongated lever arms 21 and 22. Arm 21 has a distal first zone 21a, and arms 22 also has a distal first zone 22a; and the lens is gripped between those arm zones. Arm 21 also has a pivot zone 21b rearward of and spaced from the distal zone 21a; and a third manual pressure-receiving zone 21c rearward of and spaced from the pivot zone 21b. Likewise, arm 22 has a pivot zone 22b rearward of and spaced from zone 22a, and a third manual pressure-receiving zone 22c rearward of and spaced from its pivot zone 22b. Such third zones 21c and 22c may be defined by arm segments that project toward one another, as shown, along the arm length, whereby a physician's fingers, or finger and thumb, may be easily received in and positioned by the dished or shallow pocket areas 21d and 22d, for precision control of the instrument 10 as it is used during lens implantation.

The arms are typically coupled together rearwardly of said third zones, so that the first distal zones 21a and 21b are yieldably urged toward one another by the arms to lightly but firmly grip the lens therebetween for intraocular implantation, as seen in FIG. 1. As shown, the arms are interconnected by bowed spring metal segment 25 at the rearward extents of the arms.

The said second pivot zones are configured to pivot in interengagement in response to controllable manual squeezing force exertion on the third zones 21c and 22c, thereby to cause said first zones 21a and 22a to relatively separate, freeing the lens for release in the internal eye zone. See this condition, as shown in FIG. 2.

In the example shown, there are interengageable protrusions 27 and 28 projecting between the arms at said second zones, to define mutual fulcrums for arm pivoting. The protrusions, which may be integral with the arms, have interengageable surfaces 27a and 28a which are convex toward one another, and are spaced apart, as seen in FIG. 1, prior to manual squeezing force application (see arrows 29 and 30) at the third zones. Such squeezing brings the surfaces 27a and 28a into interengagement, followed by rocking apart of the arm forward segments 21e and 22e, to allow lens release. Instead, separation of surfaces 27a and 28a allows undisturbed spring force application via the arms to the lens-gripping arm zones 21a and 22a, for precision gripping of the lens. The protrusions are close enough together that the lens is not damaged by slightly increased gripping force exertion thereon just prior to interengagement of the rocking protrusions, and subsequent lens release.

FIG. 9, steps a), b), c), and d), show progressive positions of a typical lens 17 as it releases from the instrument 10. Pivot point protrusions 32 and 33 from the arms engage the opposite sides of the gripped lens, and act as fulcrums, for lens pivoting, as it is released, and without damage to the lens. The arms 21 and 22 are shown to have substantially the same configurations that are mirror imaged with respect to a central plane 40. Note that the arms remain at opposite sides of that plane, i.e., they do not cross over one another.

FIG. 4 shows a modification wherein arm 21 has a small recess 53 formed in arm inner portion 54, for receiving the end portion 13a of a lens filamentary haptic 13, as referred to above. This controls the rear haptic position, as during lens implantation, and overcomes the problem of follow-up insertion of the rear haptic into the eye, after the lens itself has been positioned. As the released lens pivots away from the arms 21 and 22, the "trapped" rear haptic extent 13a moves out of the recess 53 and into desired position in the eye. If desired, recess 53 can be located in a protrusion 27 or 28. A single folded lens 54 is shown in FIG. 4.

FIGS. 5 and 6 show a multiple folded lens 55 having M or W shape, as seen in FIG. 6. FIG. 5 shows that lens gripped by the instrument arms 21 and 22.

Figure 7:
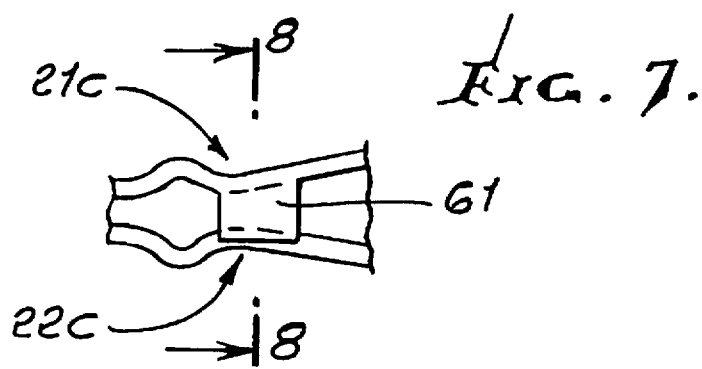
FIG. 7 is a fragmentary view of a modification in which alternate surfaces are provided on the device arms, to be gripped by a physician before the device is squeezed to release the lens.
Figure 8:
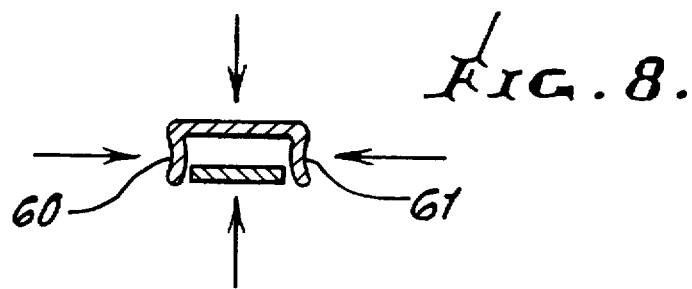
FIG. 8 is a section on lines 8—8 of FIG. 7.

FIGS. 7 and 8 show laterally spaced flanges 60 and 61 on one or both arms at the third zone, to be gripped by the user physician, as during maneuvered insertion of the arm first zones into the eye, prior to lens release. Thus, the user does not inadvertently squeeze zones 21c and 22c during such insertion. Thereafter, the user can easily shift his finger positioning 90° to engage and squeeze zones 21c and 22d, to accomplish lens release at the appropriate moment.

In this regard, the amount of squeeze or pressure on flanges 60 and 61 is not determinative of lens release, allowing the physician use more latitude or flexibility in his use of the instrument, while enhancing or facilitating ultimate precision-timing of lens release.

The method of implanting the lens into an eye zone, using the apparatus described includes:

x₁) manipulating the arms to introduce the first arm zones and the lens gripped therebetween into the eye zone, and x₂) exerting manual pressure on such third zones, exteriorly of the eye, to effect arm pivoting and separation of said first zones, thereby to release the lens into the eye.

x₃) the arms maintained at opposite sides of a plane extending through the lens and generally between the protrusions.

I claim:

1. Apparatus used for intraocular implantation of a plastic lens in an internal eye zone, as through a surgical incision in the corneo-scleral limbus, which includes:

a) two elongated lever arms, each of which has a distal first zone for gripping the lens, a second pivot zone rearward of said distal zone, and a third manual pressure receiving zone, b) said arms coupled together rearwardly of said third zones so that said first distal zones are yieldably urged toward one another by said arms to grip the lens therebetween for intraocular implantation, c) interengageable surfaces at said second pivot zones and configured to pivot in interengagement in response to controllable manual squeezing force exertion on said third zones, thereby to cause said first zones to relatively separate, freeing the lens for release in the internal eye zone, d) said arms between said first and third zones thereof remaining respectively at opposite sides of a plane extending between the arms.

2. The apparatus of claim 1 wherein there are interengageable protrusions projecting between said arms at said second zones, to define mutual fulcrums for arm pivoting.

3. The apparatus of claim 2 wherein said protrusions have interengageable surfaces which are convex toward one another.

4. The apparatus of claim 2 wherein said protrusions are spaced apart prior to said manual squeezing force exertion at said third zones.

5. The apparatus of claim 1 wherein said lever arms have configurations that are substantially the same and are mirror imaged.

6. The apparatus of claim 1 further including holder surfaces on said arms, offset from said third zones, to allow a physician to hold and manipulate the apparatus before applying said squeezing force.

7. The apparatus of claim 1, wherein said distal first zones are adapted to grip a plastic lens.

8. The claim 1 wherein said distal first zones are adapted to grip a folded lens.

9. The combination of claim 8 wherein said distal first zones are adapted to grip a folded lens having one of the following configurations:

i) U shape ii) W shape.

10. The apparatus of claim 1 including a bow spring coupling said arms together, rearwardly of said third zones.

11. The method of implanting an artificial lens into an eye zone, using the apparatus which includes a) two elongated lever arms, each of which has a distal first zone for gripping the lens, a second pivot zone rearward of said distal zone, and a third manual pressure receiving zone, b) said arms coupled together rearwardly of said third zones so that said first distal zones are yieldably urged toward one another by said arms to grip the lens therebetween for intraocular implantation, c) interengageable surfaces at said second pivot zones and configured to pivot in interengagement in response to controllable manual squeezing force exertion on said third zones, thereby to cause said first zones to relatively separate, freeing the lens for release in the internal eye zone, the steps that include:

d manipulating said arms to introduce said first arm zones and the lens gripped therebetween into said eye zone, and e exerting manual pressure on said third zones, exteriorly of the eye, to effect arm pivoting and separation of said first zones, thereby to release the lens into the eye, f the arms maintained at opposite sides of a plane extending through the lens and generally between the protrusions.

12. The apparatus of claim 1 including a recess carried by one arm proximate said first zone and located to receive the end portion of a lens haptic during lens implantation.

* * * * *